US006997887B2

(12) United States Patent
Earthman et al.

(10) Patent No.: US 6,997,887 B2
(45) Date of Patent: Feb. 14, 2006

(54) EVALUATION OF REFLECTED TIME-ENERGY PROFILE FOR DETERMINATION OF DAMPING CAPACITY

(76) Inventors: James C. Earthman, 6 Virgil Ct., Irvine, CA (US) 92612; Cherilyn G. Sheets, 22 Hermitage La., Newport Beach, CA (US) 92660

( * ) Notice: Subject to any disclaimer, the term of this patent is extended or adjusted under 35 U.S.C. 154(b) by 118 days.

(21) Appl. No.: 10/671,002

(22) Filed: Sep. 25, 2003

(65) Prior Publication Data

US 2004/0116823 A1    Jun. 17, 2004

Related U.S. Application Data

(60) Provisional application No. 60/422,186, filed on Oct. 29, 2002, provisional application No. 60/414,691, filed on Sep. 27, 2002.

(51) Int. Cl.
*A61B 5/103* (2006.01)
*A61B 19/00* (2006.01)

(52) U.S. Cl. ............... 600/590; 600/553; 73/12.01; 433/72

(58) Field of Classification Search ............... 600/587, 600/553, 552, 589, 590; 73/12.01, 573, 579; 433/72, 215; 33/513
See application file for complete search history.

(56) References Cited

U.S. PATENT DOCUMENTS

| | | |
|---|---|---|
| 3,722,100 A | 3/1973 | Weisman et al. |
| 4,341,519 A | 7/1982 | Kuhn et al. |
| 4,482,324 A | 11/1984 | Wohlgemuth |
| 4,499,906 A | 2/1985 | Wohlgemuth et al. |
| 4,689,011 A | 8/1987 | Wohlgemuth |
| 4,764,114 A | 8/1988 | Jeffcoat et al. |
| 5,144,753 A | 9/1992 | Murphy |
| 5,318,442 A | 6/1994 | Jeffcoat et al. |
| 5,518,008 A | 5/1996 | Cucchiaro et al. |
| 6,120,466 A | 9/2000 | Earthman |

OTHER PUBLICATIONS

Marc E. Levenston & Dennis R. Carter, "An Energy Dissipation-Based Model for Damage Stimulated Bone Adaptation", *Journal of Biomechanics*, vol. 31 (1998), pp. 579-586.
W. Schulte, B. d'Hoedt, D. Lukas, M. Maunz and M. Steppler "Periotest for Measuring Periodontal Characteristics-Correlation with Periodontal Bone Loss", *Journal of Periodontal Research*, 1992, vol. 27, pp. 184-190.
A. Barzin, C.G. Sheets and J.C. Earthman "Mechanical Biocompatibility of Dental Implant Materials", Proceedings of the Fourth Pacific Rim International Conference on materials, Japanese Institute of Metals, pp. 2492-2952 (2002).

(Continued)

*Primary Examiner*—Charles Marmor
(74) *Attorney, Agent, or Firm*—Knobbe, Martens, Olson & Bear LLP

(57) ABSTRACT

A method for measuring the acoustic damping capacity of a material or structure, such as a layered honeycomb structure, comprises tapping the honeycomb structure with a tapping rod. The tapping action imparts mechanical energy to the honeycomb structure. The method further comprises measuring, for a time interval, energy reflected from the honeycomb structure as a result of the tapping. The method further comprises creating a time-energy profile based on the energy reflected from the honeycomb structure during the time interval. The method further comprises evaluating the time-energy profile to determine the acoustic damping capacity of the honeycomb structure.

36 Claims, 4 Drawing Sheets

OTHER PUBLICATIONS

Ichiro Owan, David B. Burr, Charles H. Turner, Jinya Qiu, Yuan Tu, Jude E. Onyia, and Randall L. Duncan "Mechanotransduction in Bone: Osteoblasts are More Responsive to Fluid Forces than Mechanical Strain", *The American Physiological Society* (Sep. 1997), vol. 273, pp. C810-C815.

Cherilyn G. Sheets, DDS. and James C. Earthman, Ph.D., "Natural Tooth Intrusion and Reversal in Implant-Assisted Prosthesis: Evidence of and a Hypothesis for the Occurrence", *The Journal of Prosthetic Dentistry*, Dec. 1993, vol. 70, No. 6, pp. 513-520.

D. Lukas, "Periotest: Dynamically Diagnosing the Human Periodontium and the Dental Implant-Bone Interface", http://www.periotest.de/beschreibung.htm, website dated Jul. 4, 2002.

Cherilyn G. Sheets, DDS. and James C. Earthman, Ph.D., "Tooth Intrusion in Implant-Assisted Prostheses", *The Journal of Prosthetic Dentistry*, Jan. 1997, vol. 77, No. 1, pp. 39-45.

J.R. Davis, et al., Metals Handbook, vol. 17, (Metals Park, OH; ASM International, 1989), 241-244.

M.F. Ashby, "MaterialsSelection in Mechanical Design", (New York; Pergamon Press, 1992), 40.

A.B. Strong, *Fundamentals of Composites Manufacturing: Materials, Methods, and Applications*, Society of Manufacturing Engineers (1989), 92.

K.K. Chawla, *Composite Materials Science and Engineering*, (New York: Springer-Verlag, 1987), 229-258.

B.J. Lazan, "Damping of Materials and Members in Structural Mechanics", Pergamon Press, New York (1968).

J. Zhang, et al., "Effects of Secondary Phases on the Damping Behavior of Metals, Alloys and Metal Matrix Composites", Materials Science and Engineering Reviews, R13, No. 8, Dec. 1994.

S. Kalpakjian, "Manufacturing Engineering and Technology", Addison-Wesley (1992).

D.A. Brenner et al., "Novel Instrumentation for Quantitive Determination of Energy Damping in Materials and Structures", Scripta Metallurgica et Materialia, vol. 13, No. 4, pp. 467-470, 1994.

Operating Instructions for "PERIOTEST—for you by Siemens", Siemens Corporation, pp. 1-11.

E.J. Graesser et al, Reprt Nol DTRC-SME-91/05, David Taylor Research Center, Annapolis, Maryland (1991).

B.D. Stanley, et al. "Nondestructive Evaluation and Materials Properties III, The Minerals, Metals Materials Society", 1997.

EVALUATION OF REFLECTED TIME-ENERGY PROFILE FOR DETERMINATION OF DAMPING CAPACITY

PRIORITY APPLICATIONS

This application claims the benefit of U.S. Provisional Application 60/414,691 (filed 27 Sep. 2002), and U.S. Provisional Application 60/422,186 (filed 29 Oct. 2002). The entire disclosure of both of these priority applications is hereby incorporated by reference herein.

FIELD OF THE INVENTION

The present invention relates generally to evaluation of the mechanical properties of an object, and more specifically relates to evaluation of a time-energy profile response from the object after an impact thereon.

BACKGROUND OF THE INVENTION

When an object is subjected to an impact force, a stress wave is transmitted through the object. This stress wave causes deformations in the internal structure of the object. As the object deforms it acts, in part, as a shock absorber, dissipating a portion of the mechanical energy associated with the impact. The ability of the object to dissipate mechanical energy, commonly referred to as the "damping capacity" of the object, depends on several factors, including the type and structural integrity of the materials comprising the object.

Instruments have been developed that are capable of quantitatively measuring the damping capacity of an object. An example of such an instrument is described in U.S. Pat. No. 6,120,466 ("the '466 patent"), issued 19 Sep. 2000 and entitled "System and Method for Quantitative Measurements of Energy Damping Capacity," the entire disclosure of which is hereby incorporated by reference herein. The instrument disclosed in the '466 patent provides an objective, quantitative measurement of the damping capacity of an object, referred to as the loss coefficient η. The energy of an elastic wave attenuates relatively quickly in materials with a relatively high loss coefficient, whereas the energy of an elastic wave attenuates relatively slowly in materials with a relatively low loss coefficient.

The damping capacity of an object is an important parameter in a wide variety of applications. For example, in the field of dentistry, when a healthy tooth is subjected to an impact force, the mechanical energy associated with the impact is primarily dissipated by the periodontal ligament. Changes in the structure of the periodontal ligament that reduce its ability to dissipate the mechanical energy associated with an impact force, and thus reduce overall tooth stability, can be detected by measuring the loss coefficient of the tooth.

SUMMARY OF THE INVENTION

While evaluation of the loss coefficient provides a quantitative parameter corresponding to the damping capacity of an object, the loss coefficient alone does not provide complete information regarding the structural integrity of an object. Additional information can be provided by evaluating the time-energy profile as the object is subjected to an impact force. For example, materials that deform uniformly will exhibit a time-energy profile having a smooth, symmetric, bell shape. In contrast, nonuniform materials or materials having internal defects will cause the time-energy profile to be asymmetric.

In accordance with the foregoing, in one embodiment of the present invention, a method for measuring the acoustic damping capacity of a layered honeycomb structure comprises tapping the honeycomb structure with a tapping rod. The tapping action imparts mechanical energy to the honeycomb structure. The method further comprises measuring, for a time interval, energy reflected from the honeycomb structure as a result of the tapping. The method further comprises creating a time-energy profile based on the energy reflected from the honeycomb structure during the time interval. The method further comprises evaluating the time-energy profile to determine the acoustic damping capacity of the honeycomb structure.

According to another embodiment of the present invention, a method for measuring the damping capacity of a prosthetic dental implant structure to determine the stability of the implant structure comprises tapping the implant structure with a tapping rod. The tapping action imparts mechanical energy to the implant structure. The method further comprises measuring, for a time interval, energy reflected from the implant structure as a result of the tapping. The method further comprises creating a time-energy profile based on the energy reflected from the implant structure during the time interval. The method further comprises evaluating the time-energy profile to determine the damping capacity of the implant structure.

According to another embodiment of the present invention, a method for measuring the damping capacity of a tooth to assess the tooth health comprises tapping the tooth with a tapping rod. The tapping action imparts mechanical energy to the tooth. The method further comprises measuring, for a time interval, energy reflected from the tooth as a result of the tapping. The method further comprises creating a time-energy profile based on the energy reflected from the tooth during the time interval. The method further comprises evaluating the time-energy profile to determine the damping capacity of the tooth.

According to another embodiment of the present invention, a method for determining a damping capacity of an object comprises tapping the object with a tapping rod. The tapping action imparts mechanical energy to the object. The method further comprises measuring, for a time interval, energy reflected from the object as a result of the tapping. The method further comprises creating a time-energy profile based on the energy reflected from the object during the time interval. The method further comprises evaluating the time-energy profile to determine the damping capacity of the object.

According to another embodiment of the present invention, a method comprises tapping an object, thereby imparting mechanical energy to the object. The method further comprises measuring energy reflected from the object as a result of the tapping. The method further comprises creating a time-energy profile of the energy reflected from the object. The method further comprises evaluating the time-energy profile to make a determination regarding the structural characteristics of the object.

According to another embodiment of the present invention, a system for providing information regarding the damping capacity of an object comprises a test probe housing a movable impact rod. The test probe is mounted against the object. The system further comprises an accelerometer configured to detect energy reflected from the object after the impact rod impacts the object. The system further comprises a computer coupled to the accelerometer. The computer is configured to generate and display a time-energy profile of the reflected energy as detected by the accelerometer.

BRIEF DESCRIPTION OF THE DRAWINGS

Exemplary embodiments of the damping capacity evaluation system are illustrated in the accompanying drawings, which are for illustrative purposes only. The drawings comprise the following figures, in which like numerals indicate like parts.

DETAILED DESCRIPTION OF PREFERRED EMBODIMENTS

The systems described herein comprise hardware and virtual instrumentation software capable of analyzing the energy dissipation characteristics of a specimen. The energy dissipation information provided by these systems and methods provides objective information that is relevant to the evaluation and design of a wide variety of mechanical structures, such as natural and prosthetic dental structures and engineering structures. Such information is also useful in the study of materials and composites.

Figure 1:
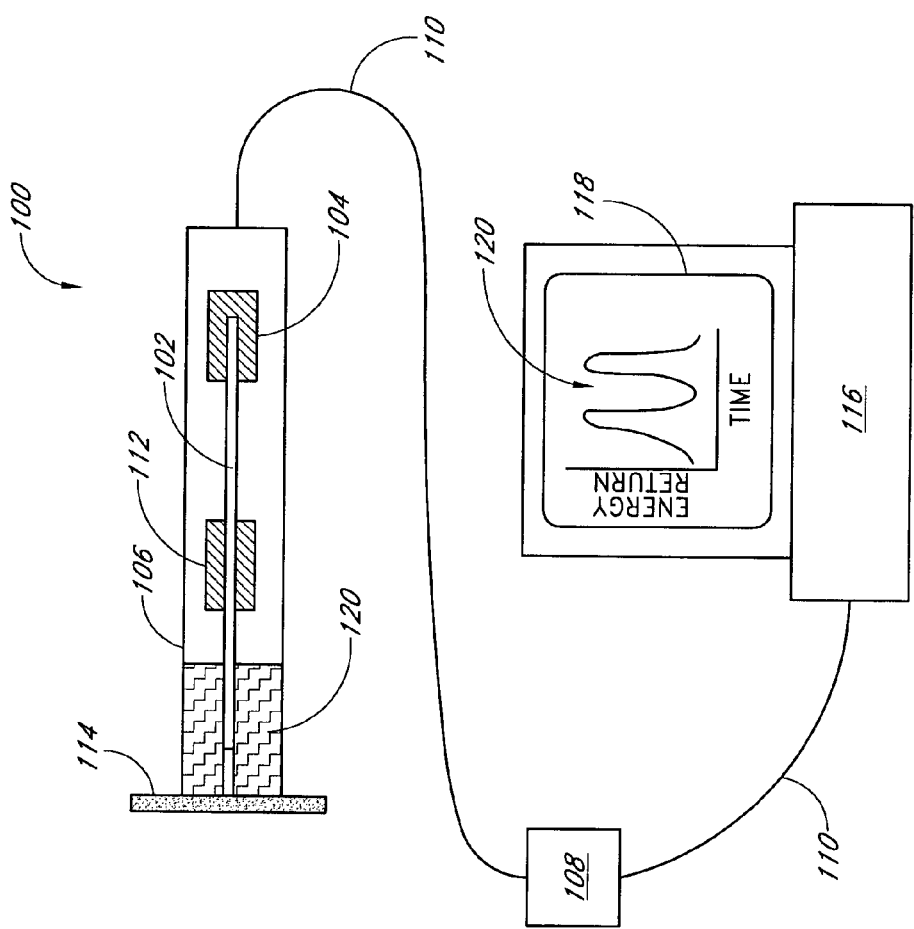
FIG. 1 is a schematic illustration of an exemplary energy dissipation test system.

An exemplary energy dissipation test system is illustrated in FIG. 1. This system comprises a percussion instrument 100 having a movable tapping rod 102 mounted within a housing 106. In one embodiment, the percussion instrument 100 comprises a Periotest®, available from Medizintechnik Gulden AG (Bensheim, Germany). In a modified embodiment, the percussion instrument comprises a Periotest® that has been modified as described in the '466 patent, thereby allowing more accurate and reproducible measurements to be performed. For example, outfitting the Periotest® with a polytetrafluoroethylene ("PTFE") sleeve 120 configured to be placed against a specimen 114 can increase the accuracy and reproducibility of measurements. In other embodiments, other types of percussion instrumentation can be used.

Still referring to FIG. 1, the percussion instrument 100 is configured to be placed against a specimen 114 for which energy dissipation analysis is to be performed. To test the specimen 114, the tapping rod 102 is impacted against the specimen 114 one or more times. For example, in one embodiment, the tapping rod impacts the specimen 114 approximately sixteen times in a period of four seconds. In other embodiments, faster or slower impact repetition rates are used. In an exemplary embodiment, the tapping rod 102 is driven by one or more propulsion coils 112 electronically activated by a finger switch (not shown), although the propulsion coils 112 can be activated remotely in other embodiments.

When the tapping rod 102 impacts the specimen 114, some of the kinetic energy of the tapping rod 102 is converted to mechanical energy propagating through the specimen 114 as a stress wave. Most of the remaining of the kinetic energy is converted (dissipated) to heat, as dictated by the loss coefficient and structure of the specimen. A portion of the propagated mechanical energy is reflected back to the tapping rod 102, where it can be detected by an accelerometer 104 mounted within the housing 106. The accelerometer 104 produces signals that correspond to the reflected mechanical energy resulting from the impact between the tapping rod 102 and the specimen 114.

Still referring to the exemplary embodiment illustrated in FIG. 1, the signals generated by the accelerometer 104 are provided to a data acquisition board housed in a computer 116 via an instrumentation interface 108. In one embodiment, the instrumentation interface 108 comprises a signal conditioner and an independent power supply. In a modified embodiment, the instrumentation interface is incorporated within the computer. In an exemplary embodiment, the data acquisition board comprises a sixteen bit analog to digital converter channel. In such embodiments, the computer 116 operates at a sampling rate of at least about 800 kHz; although in other embodiments, the computer 116 operates at a sampling rate of at least about 500 kHz. The signals can be transmitted from the accelerometer 104 to the computer 116 via a coaxial cable 110, or via another signal transport mechanism.

In the illustrated embodiment, the computer 116 includes virtual instrumentation software capable of analyzing the signals received from the accelerometer 104. A wide variety of different types of data acquisition software can be used to acquire data from the accelerometer 104. In one embodiment, customized data acquisition software developed using the LabVIEW programming environment, available from National Instruments (Austin, Tex.), is used, although other programming environments can be used in other embodiments.

After the signals are received from the accelerometer 104, the data processing software is capable of quantitatively measuring the damping capacity of the specimen 114, which is often expressed in terms of the loss coefficient $\eta$. For a series of impacts, as described above, several calculations of the damping capacity can be performed. For example, in one embodiment the tapping rod 102 impacts the specimen 114 sixteen times, and the damping capacity of the specimen is calculated for ten of the sixteen impacts. In such embodiments, the standard deviation of the damping capacity measurements can be calculated, thereby providing the user with an indication of the accuracy of the measurements. Specifically, if the percussion instrument 100 was not properly aligned with the specimen 114, or if another source of error was introduced into the measurement process, this error will likely manifest itself in the form of a elevated standard deviation of a series of damping capacity measurements.

Further discussion of the loss coefficient and methods for its calculation based on data generated by percussion instrumentation, including details on method for calibrating percussion instrumentation, can be found in the '466 patent.

Still referring to the exemplary embodiment illustrated in FIG. 1, the computer 116 further comprises memory registers, such that the amount of energy reflected from the specimen 114 at several points over a discrete time period can be recorded. In such embodiments, the energy returned from the specimen 114 can be plotted as a function of time on a display 118 attached to the computer 116. This configuration allows the user to view and analyze the time-energy profile 120 of the energy reflected from the specimen 114.

In addition to generation of a time-energy profile 120, other analyses can also be performed on the signals returned from the accelerometer 104. For example, the amount of work W associated with the impact can be evaluated by integrating the force F applied to the tapping rod 102 with respect to the displacement of the specimen $U_s$. That is, $$W=\int F \cdot du_s.$$

The force F applied to the tapping rod 102 during its impact with the specimen 114 can be measured using the accelerometer 104. After the impact, the amount of work depends partially on the quantity of defects present in the specimen 114. In particular, defects in the specimen 114 dissipate the kinetic energy of the rod as it impacts the specimen 114, thereby reducing the amount of elastic energy available to be returned to the tapping rod 102. A comparison of the amount of elastic energy returned to the tapping rod 102 and the total work W associated with the impact can be used to determine the quantity and nature of structural defects present in the specimen 114.

Exemplary Application: Natural and Prosthetic Dental Structures

As described above, the mechanical energy associated with an impact against a natural tooth is primarily dissipated by the periodontal ligament. More specifically, when a tooth is subjected to an impact force, a stress wave is transmitted through the tooth and into the periodontal ligament, which functions to connect the tooth to the underlying bone. Because of the way it deforms, the periodontal ligament acts as a shock absorber, dissipating much of the energy associated with the impact. This damping process advantageously reduces the resultant impact force transmitted to the surrounding bone. In contrast, dental implant prostheses often have no mechanism by which to dissipate significant amounts of mechanical energy because of the nature of the materials used. Thus, mechanical energy tends to pass from an implant structure to the underlying bone with relatively little damping. This difference in mechanical behavior may be particularly critical for people who habitually brux and/or clench their teeth, since such behavior imparts relatively large impact forces on teeth.

The relative extent to which a material dissipates elastic mechanical energy can be characterized using the loss coefficient η, as discussed previously. Loss coefficient values have been determined for natural teeth, as well as for a wide variety of implant-supported superstructures, such as superstructures made of resin matrix composites, gold alloys, and porcelain fused to gold laminates. Implant-supported structures typically dissipate less mechanical energy than their natural tooth counterparts. However, the ability of an implant to dissipate mechanical energy depends on the level of osseointegration around the implant: poor osseointegration between an implant and the surrounding bone can cause abnormally high levels of energy dissipation. Thus, energy dissipation initially increases after placing an implant, but then usually decreases as osseointegration progresses. Eventually, the energy dissipation (damping) capacity of the implant becomes constant as the osseointegration process progresses to completion.

Healthy teeth and well-integrated implants exhibit a low level of energy dissipation with a smooth, symmetric, bell-shaped time-elastic energy profile. As used in this context, the term "elastic energy" refers to the elastic energy imparted to the tapping rod 102 of the percussion instrument 100. The elastic energy $E_e$ is given by $E_e = k \cdot F^2$, where the constant k varies inversely with the effective elastic modulus of the tapping rod 102 and where the force F is proportional to both the mass of the tapping rod 102 and the maximum deceleration of the tapping rod 102 as a result of the stress wave created from the impact.

Figure 2:
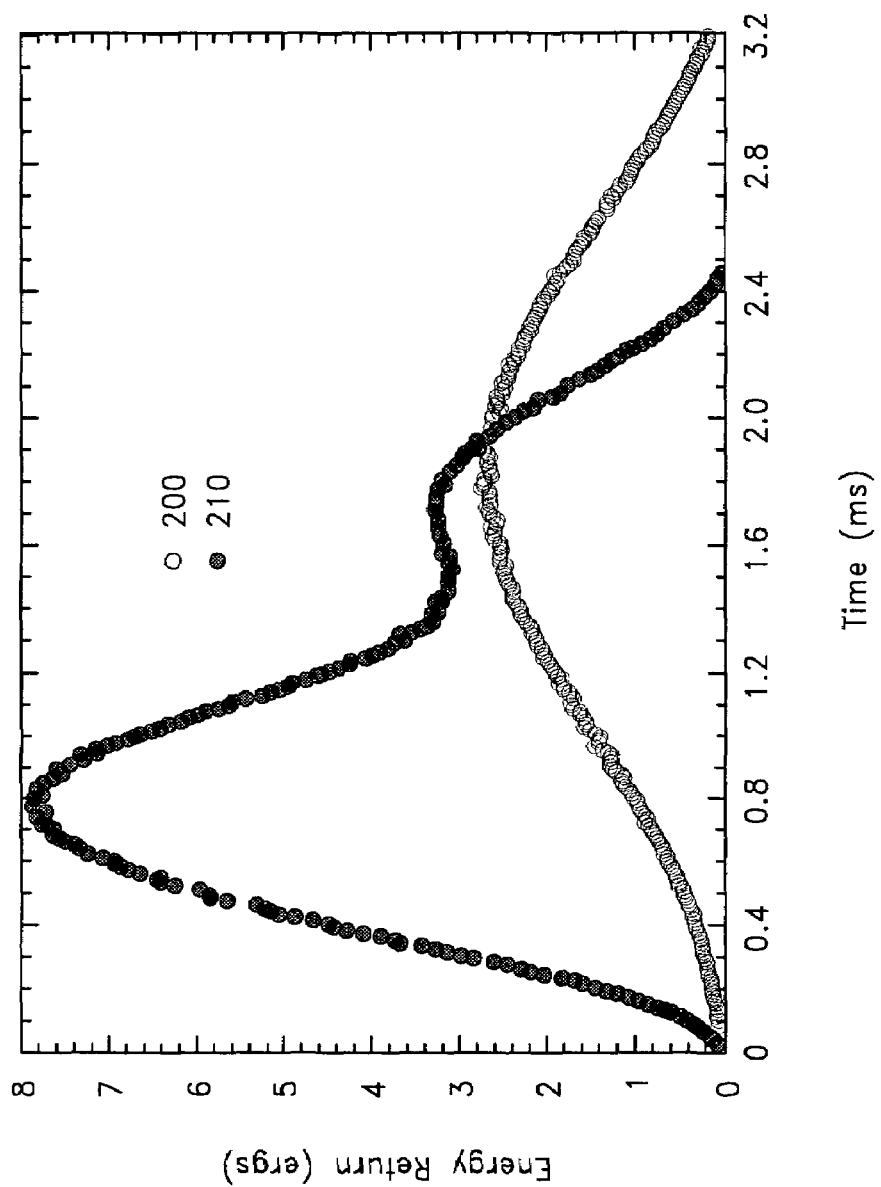
FIG. 2 illustrates time-energy profiles for a healthy tooth (200) and an implant that is not well-integrated (210).

In contrast to well-integrated implants, implants suffering from poor osseointegration, bone loss, internal defects, or a damaged structure will typically exhibit a nonuniform time-energy profile. For example, FIG. 2 illustrates a "normal" time-energy profile 200 for a healthy tooth, as well as an "abnormal" time-energy profile 210 for an implant structure that is not well-integrated. As illustrated, the time-energy profile 200 for the healthy tooth has a smooth, symmetric, bell shape, whereas the time-energy profile 210 for the abnormal implant structure is not smooth and symmetric, and has a secondary maxima 212. The shape of the time-energy profile for the abnormal implant structure indicates that defects, such as loose screws, a damaged internal structure, bone loss at the bone/implant interface, or poor osseointegration, are present. In addition to secondary maxima, other abnormalities in the shape of the time-energy profile that are indicative of structural defects include scattered data, asymmetries and irregular shapes.

Figure 3:
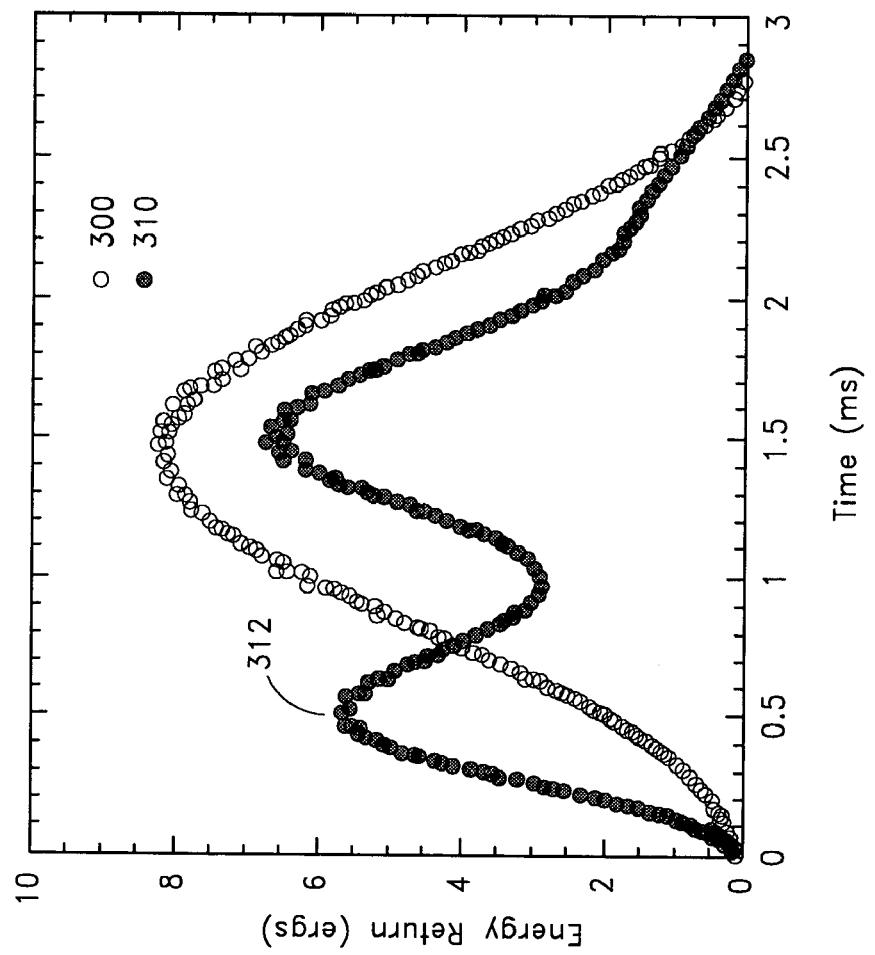
FIG. 3 illustrates time-energy profiles for a well-integrated implant (300) and an implant that is not well-integrated (310).

An additional example of this principle is provided in FIG. 3, which illustrates a "normal" time-energy profile 300 of a well-integrated implant, as well as an "abnormal" time-energy profile 310 for an implant structure that is not well-integrated. Both of these implant structures are located in the mouth of a heavily parafunctional elderly patient. As explained previously, the presence of the secondary maxima 312 indicates that defects, such as loose screws, a damaged internal structure, bone loss at the bone/implant interface, or poor osseointegration, are present at the implant site.

The foregoing examples illustrate that analysis of the time-energy profile of a dental structure can provide information about the integrity and stability of that structure. These analysis techniques provide clinicians with an accurate, fast and simple tool that provides information on the stability of natural and prosthetic dental structures without requiring an invasive procedure.

Exemplary Application: Composite Structures

The percussion instrumentation described above can also be used in fields other than dentistry. For example, such instrumentation can be used in assessing the local damping capacity of composite structures, such as layered honeycomb composites. In particular, use of such instrumentation in the testing of composite structures advantageously allows the damping capacity of these structures to be evaluated without damaging the structures. The instrumentation disclosed herein is also light, portable, easy to use, quick and inexpensive as compared to conventional apparatuses for evaluating damping capacity.

Because damping capacity measures the ability of a material to absorb and isolate vibration, damping capacity is of particular interest with respect to materials used for acoustic insulation, such as in the aerospace, boating, civil engineering and automotive engineering fields. Thus it is often sought to test the damping capacity of new materials under development, as well as conventional materials after sustained use.

As an example, layered honeycomb structures generally have a relatively high damping capacity, and thus are often used as acoustic insulators in these fields. Typical layered honeycomb structures have two relatively thin facings that have high strength and stiffness. The facings enclose a honeycomb core structure that is relatively thick, but lightweight and with high strength in the direction perpendicular to the facings. For example, the honeycomb core structure can comprise a Nomex® honeycomb core, available from E.l. du Pont de Nemours and Company (Wilmington, Del.). The facings and the core are generally bonded together, either mechanically or with adhesives (such as, for example, with a phenolic resin), thus giving the structure composite properties. In the composite structure, the facings carry bending stresses, while the core carries shear stresses. When exposed to acoustic vibrations for a prolonged period, degradation in the bonds between the layers, as well as in the honeycomb core itself, can cause a layered honeycomb core structure to have diminished acoustic insulation capacity.

Figure 4:
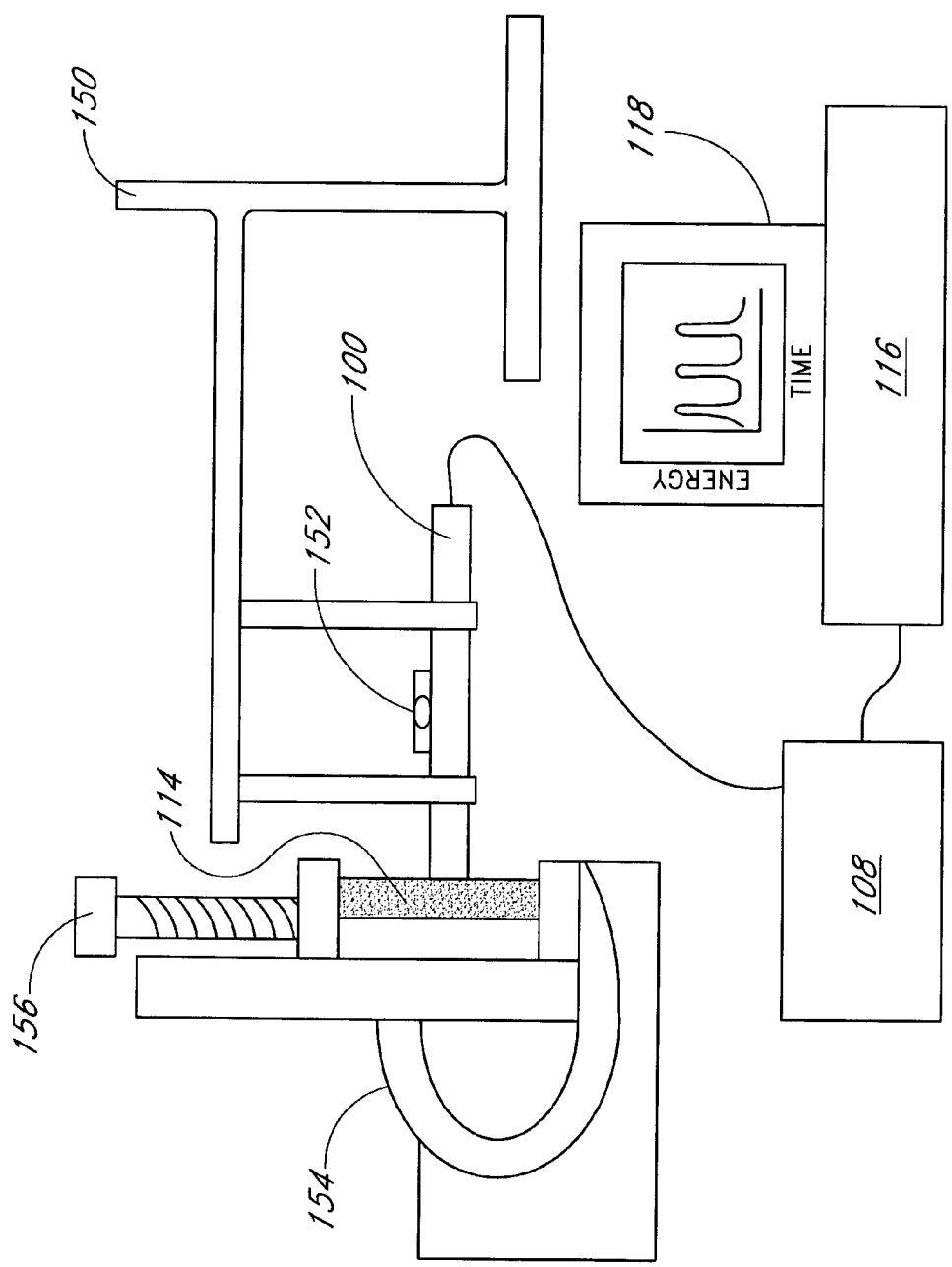
FIG. 4 illustrates an exemplary embodiment of an apparatus configured for evaluating the damping capacity of composite structures.

Referring now to FIG. 4, an exemplary embodiment of an apparatus configured for evaluating the damping capacity of composite structures is illustrated. The apparatus comprises a percussion instrument 100 mounted within a secured bracket 150 configured to stabilize the percussion instrument 100. The percussion instrument 100 is optionally outfitted with a level 152 to assist in aligning the percussion instrument 100 substantially perpendicular to a specimen 114 that is to be tested. In an exemplary embodiment, the specimen 114 is mounted in an angle vise 154 having a hand-adjustable vise drive 156, thereby allowing the specimen 114 to be held in compression during testing. In a modified embodiment, the angle vise 154 is outfitted with rubber grips to reduce external sources of vibrational noise that could be detected by the percussion instrument 100.

Still referring to FIG. 4, and similar to the configuration illustrated in FIG. 1, the percussion instrument 100 is electronically connected to a computer 116 via an instrumentation interface 108. In such embodiments, the computer 116 comprises a display 118 capable of graphically presenting data generated by the percussion instrument 100, such as a time-energy profile.

The testing apparatus illustrated in FIG. 4 can be used to evaluate the damping capacity of a wide variety of materials. For example, in one application, this apparatus can be used to evaluate the damping capacity of layered honeycomb composite specimens. In such an application, the specimen 114 to be tested is mounted in the angle vise 154, which is tightened using the vise drive 156 to a torque of approximately 2765 g·cm, although in other embodiments, the specimen 114 can be loaded to a different torque.

The percussion instrument 100 is then positioned at approximately the center of the specimen 114 in an orientation that is approximately perpendicular to one of the outer facings of the specimen 114. As described above, in certain configurations, a level can be used to assist in aligning the percussion instrument 100 and the specimen 114 in a substantially perpendicular orientation. In one embodiment, the end of the percussion instrument 100 that is placed against the specimen 114 comprises a Teflon® tip having a diameter of approximately 2.5 cm. This design aids in aligning the specimen 114 with the percussion instrument 100, as well as in reducing external sources of vibrational noise that could be detected by the percussion instrument 100.

As described above, the percussion instrument 100 is configured to impact a tapping rod against the specimen 114. In one testing configuration, the tapping rod impacts the specimen 114 sixteen times in four seconds, with each impact causing vibrational energy to be reflected back to the tapping rod, where it is detected by the accelerometer, which generates a signal that is sent to the computer 116. The computer 116 can be configured to analyze the reflected energy associated with all or a portion of the impacts. For example, in one testing configuration, the computer 116 analyzes the reflected energy for ten of the sixteen impacts. The computer analysis can comprises analysis intended to provide the user with information regarding the acoustic damping properties of the specimen 114, such as a time-energy profile of the elastic or work energy associated with the percussion of the tapping rod 102 against the specimen 114.

Using the exemplary testing parameters set forth above, wherein the tapping rod is configured to impact the specimen 114 sixteen times in four seconds, the duration of each percussion response was approximately 0.6 milliseconds, which corresponds to a vibration loading frequency of approximately 1700 Hz. In other embodiments, the percussion response can be manipulated to simulate different vibration loading frequencies.

SCOPE OF THE INVENTION

While the foregoing detailed description discloses several embodiments of the present invention, it should be understood that this disclosure is illustrative only and is not limiting of the present invention. It should be appreciated that the specific configurations and operations disclosed can differ from those described above, and that the methods described herein can be used in contexts other than evaluation of dental structures.

We claim:

1. A method for measuring the acoustic damping capacity of a layered honeycomb structure, the method comprising:
    tapping the honeycomb structure with a tapping rod, thereby imparting mechanical energy to the honeycomb structure;
    measuring, for a time interval, energy reflected from the honeycomb structure as a result of the tapping;
    creating a time-energy profile based on the energy reflected from the honeycomb structure during the time interval; and
    evaluating a shape of the time-energy profile to determine the acoustic damping capacity of the honeycomb structure.

2. A method for measuring the damping capacity of a prosthetic dental implant structure to determine the stability of the implant structure, the method comprising:
    tapping the implant structure with a tapping rod, thereby imparting mechanical energy to the implant structure;
    measuring, for a time interval, energy reflected from the implant structure as a result of the tapping;
    creating a time-energy profile based on the energy reflected from the implant structure during the time interval; and
    evaluating a shape of the time-energy profile to determine the damping capacity of the implant structure.

3. A method for measuring the damping capacity of a tooth to assess the tooth health, the method comprising:
    tapping the tooth with a tapping rod, thereby imparting mechanical energy to the tooth;
    measuring, for a time interval, energy reflected from the tooth as a result of the tapping;
    creating a time-energy profile based on the energy reflected from the tooth during the time interval; and
    evaluating a shape of the time-energy profile to determine the damping capacity of the tooth.

4. A method for determining a damping capacity of an object, the method comprising:
    tapping the object with a tapping rod, thereby imparting mechanical energy to the object;

measuring, for a time interval, energy reflected from the object as a result of the tapping;

creating a time-energy profile based on the energy reflected from the object during the time interval; and evaluating a shape of the time-energy profile to determine the damping capacity of the object.

5. The method of claim 4, wherein evaluating the time-energy profile further comprises evaluating the symmetry of a pulse of energy reflected from the object.

6. The method of claim 4, wherein evaluating the time-energy profile further comprises counting the number of energy maxima reflected after the object is tapped.

7. The method of claim 4, wherein evaluating the time-energy profile further comprises evaluating a force applied to the tapping rod during tapping as a function of displacement of the object.

8. The method of claim 4, wherein the tapping rod is positioned within a housing that is mounted in contact with the object.

9. The method of claim 4, wherein the tapping rod is oriented substantially perpendicular with respect to a surface of the object.

10. The method of claim 4, wherein the object is held in compression during the tapping.

11. A method comprising:

tapping an object, thereby imparting mechanical energy to the object;

measuring energy reflected from the object as a result of the tapping;

creating a time-energy profile of the energy reflected from the object; and evaluating a shape of the time-energy profile to make a determination regarding the structural characteristics of the object.

12. The method of claim 11, wherein the object is held in compression during the tapping.

13. The method of claim 11, wherein evaluating the time-energy profile further comprises evaluating the symmetry of a reflected energy pulse.

14. The method of claim 11, wherein a cylindrical tapping rod is used to tap the object.

15. The method of claim 11, wherein a cylindrical tapping rod is used to tap the object, and wherein the tapping rod is oriented substantially perpendicular with respect to a surface of the object.

16. The method of claim 11, wherein a cylindrical tapping rod is used to tap the object, and wherein the tapping rod is positioned within a housing that is mounted in contact with the object.

17. The method of claim 11, wherein evaluating the time-energy profile further comprises counting the number of energy maxima reflected after the object is tapped.

18. The method of claim 11, wherein evaluating the time-energy profile further comprises making a determination of the damping capacity of the object.

19. The method of claim 11, wherein evaluating the time-energy profile further comprises evaluating a force applied to the tapping rod during tapping as a function of displacement of the object.

20. The method of claim 11, wherein the object is a tooth.

21. The method of claim 11, wherein the object is a prosthetic dental implant structure.

22. The method of claim 11, wherein the object comprises a layered honeycomb structure.

23. A system for providing information regarding the damping capacity of an object, the system comprising:

a test probe housing a movable impact rod, the test probe mounted against the object;

an accelerometer configured to detect energy reflected from the object after the impact rod impacts the object;

a data analyzer programmed to evaluate a shape of a reflected energy pulse detected by the accelerometer; and a computer coupled to the accelerometer, the computer configured to generate and display a time-energy profile of the reflected energy as detected by the accelerometer.

24. The system of claim 23, wherein the object is a tooth.

25. The system of claim 23, wherein the object is a prosthetic dental implant structure.

26. The system of claim 23, wherein the object comprises a layered honeycomb structure.

27. The system of claim 23, wherein the data analyzer is further programmed to count the number of energy maxima reflected after the impact rod impacts the object.

28. The system of claim 23, wherein the impact rod is oriented substantially perpendicular with respect to a surface of the object.

29. The system of claim 23, further comprising a vise configured to hold the object in compression when the impact rod impacts the object.

30. A method comprising:

tapping a structure with a tapping rod, thereby imparting mechanical energy to the structure, wherein the structure is anchored in a foundation;

measuring energy reflected from the structure as a result of the tapping;

creating a time-energy profile of the energy reflected from the structure; and evaluating a shape of the time-energy profile to make a determination regarding the stability of the structure in the foundation.

31. The method of claim 30, wherein the determination regarding the stability of the structure in the foundation is a level of osseointegration of the structure within the foundation.

32. The method of claim 30, wherein the structure is a medical implant structure implanted into a patient's body.

33. The method of claim 30, wherein the structure is a dental implant structure.

34. The method of claim 30, wherein evaluating the time-energy profile further comprises evaluating the symmetry of a pulse of energy reflected from the object.

35. The method of claim 30, wherein evaluating the time-energy profile further comprises counting the number of energy maxima reflected after the object is tapped.

36. The method of claim 30, wherein the foundation is a ligament structure.

* * * * *